US00PP28042P3

(12) United States Plant Patent
Carter

(10) Patent No.: US PP28,042 P3
(45) Date of Patent: May 16, 2017

(54) ***SALVIA* PLANT NAMED 'ELK WHITE ICE'**

(50) Latin Name: ***Salvia greggii*×*S. microphylla***
Varietal Denomination: Elk White Ice

(71) Applicant: Kermit E. Carter, Elk, CA (US)

(72) Inventor: Kermit E. Carter, Elk, CA (US)

( * ) Notice: Subject to any disclaimer, the term of this patent is extended or adjusted under 35 U.S.C. 154(b) by 71 days.

(21) Appl. No.: 14/545,436

(22) Filed: May 4, 2015

(65) Prior Publication Data

US 2016/0330896 P1 Nov. 10, 2016

(51) Int. Cl.
*A01H 5/02* (2006.01)

(52) U.S. Cl.
USPC ..... Plt./475

(58) Field of Classification Search
USPC ..... Plt./475
See application file for complete search history.

(56) References Cited

PUBLICATIONS

Houzz Has anyone ordered form 'Flowers by the Sea'? Oct. 2014, retrieved on Sep. 7, 2016, retrieved from the Internet at <http://forums.gardenweb.com/discussions/2149497/has-has-anyone-ordered-from-flowers-by-the-sea> 5 pp.*

* cited by examiner

*Primary Examiner* — June Hwu
(74) *Attorney, Agent, or Firm* — Bethany R. Roahrig; Barbara Campbell; Cochran Freund & Young, LLC

(57) ABSTRACT

A new cultivar of *Salvia* named 'Elk White Ice' that is distinguishable by its compact upright plant habit, profuse branching and secondary branching, and pure white flowers, is disclosed.

3 Drawing Sheets

Genus and species: *Salvia greggii*×*S. microphylla*.
Variety denomination: 'Elk White Ice'.

BACKGROUND

The present disclosure relates to a new and distinct cultivar of *Salvia* plant, also known as a sage, a perennial that is grown for use as an ornamental landscape and container plant. The new variety is a hybrid of *Salvia greggii* and *Salvia microphylla* and will be referred to hereinafter by the cultivar name 'Elk White Ice'.

'Elk White Ice' originated and was selected from a large population of hybrid seedlings from a *Salvia* breeding program which was started in 2009. The breeding program was conducted in a greenhouse nursery in Elk, Calif. A controlled hybridization was carried out in 2012 between *Salvia greggii* 'Texas Wedding' (unpatented) as the female parent and *Salvia microphylla* 'Robin Middleton' (unpatented) as the male parent.

Seeds from this hybridization were sown and a single plant was selected in 2013 for its pure white flowers and naturally compact and branching and secondary branching habit, and was subsequently named 'Elk White Ice'.

'Elk White Ice' was first asexually propagated in early spring of 2013 in a greenhouse at the inventors nursery in Elk, Calif. using softwood tip cuttings. 'Elk White Ice' is stable and reproduces true to type in successive generations of asexual reproduction.

SUMMARY

The following traits have been repeatedly observed and represent the distinguishing characteristics of 'Elk White Ice'. 'Elk White Ice' has not been tested under all possible conditions and phenotypic differences may be observed with variations in environmental, climatic, and cultural conditions, without however, any variance in genotype.

1. 'Elk White Ice' exhibits a compact upright plant habit;
2. 'Elk White Ice' branches profusely with secondary branches appearing in pairs at each node of the primary branches.
3. The flowers of 'Elk White Ice' are pure white in color; and
4. 'Elk White Ice' grows and flowers rapidly. Flowering plants may be produced in 10 to 12 weeks from a cutting.

DESCRIPTION OF THE PHOTOGRAPHS

The accompanying color photographs illustrate the overall appearance of the new *Salvia* cultivar 'Elk White Ice' showing the colors as true as it is reasonably possible to obtain in colored reproductions of this type. Photographs were taken in April, 2015 in Santa Barbara, Calif. of three-month old plants grown outdoors in quart containers, with one pinch after initial cutting establishment and without any chemical growth regulators. Colors in the photographs may differ from the color values cited in the detailed botanical description, which more accurately describes the actual colors of the new variety 'Elk White Ice'.

DESCRIPTION OF THE NEW VARIETY

Figure 1:
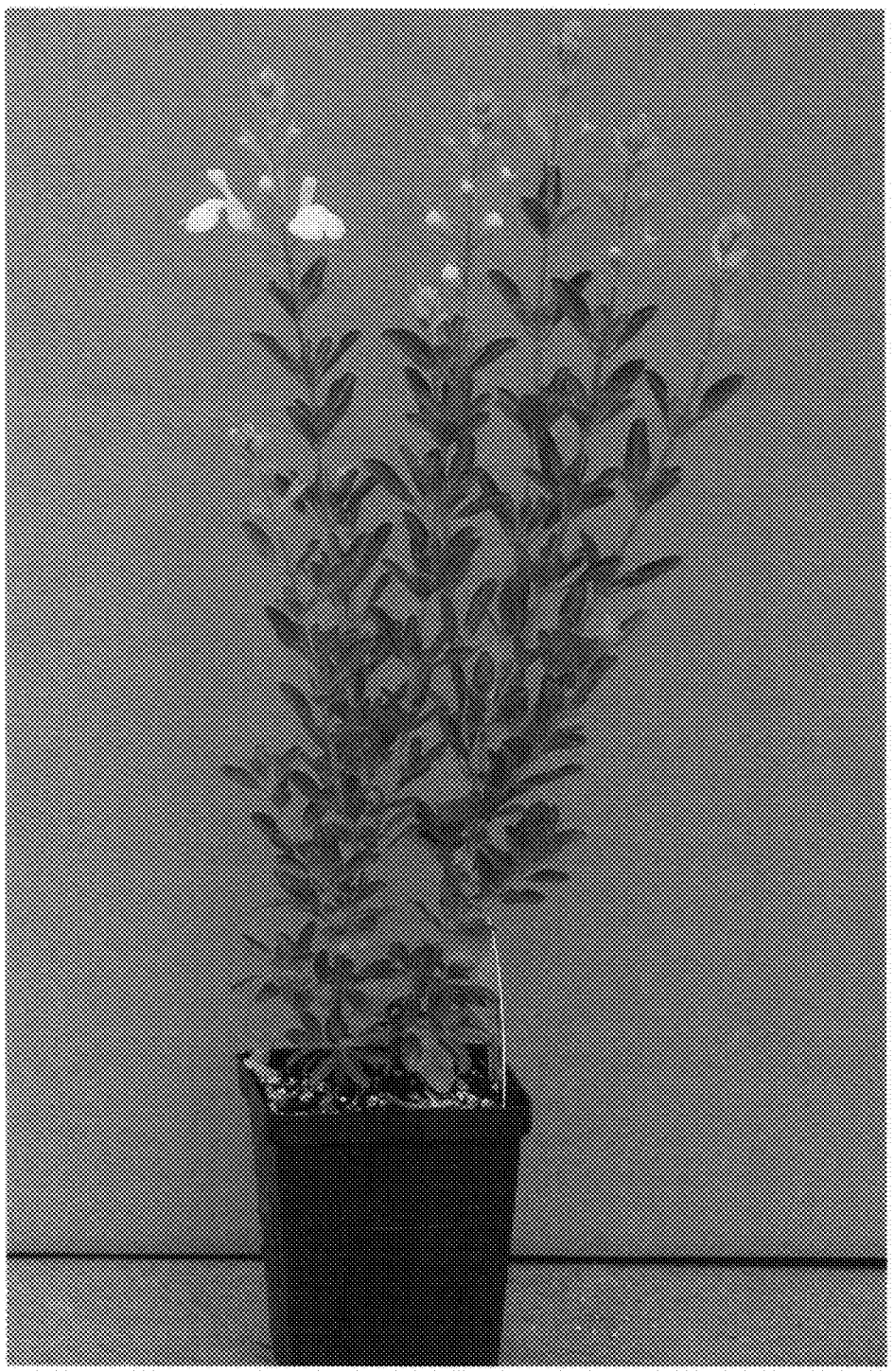
FIG. 1 depicts an entire plant in flower of 'Elk White Ice'.
Figure 2:
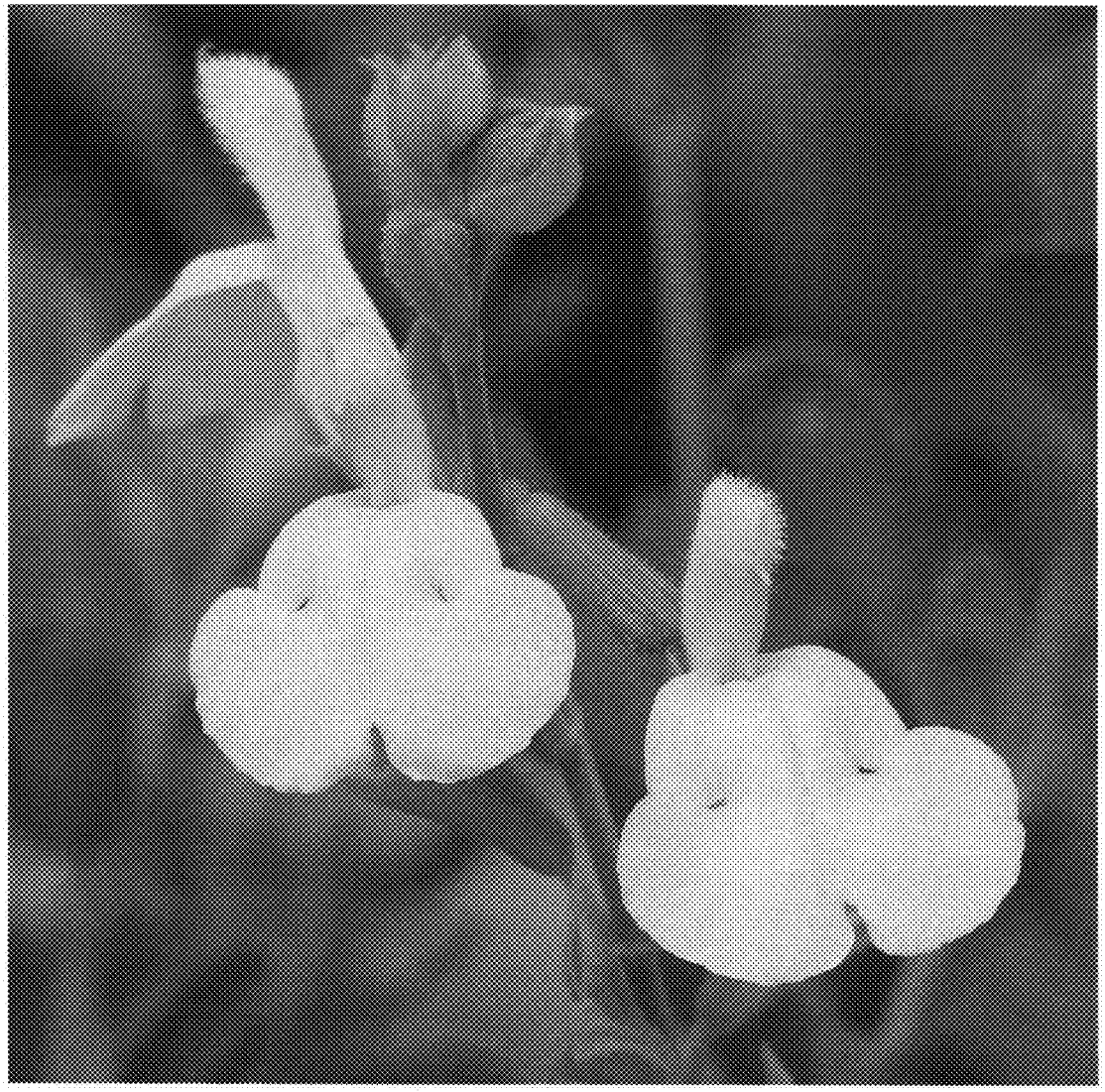
FIG. 2 depicts a close-up view of the inflorescence of 'Elk White Ice'.
Figure 3:
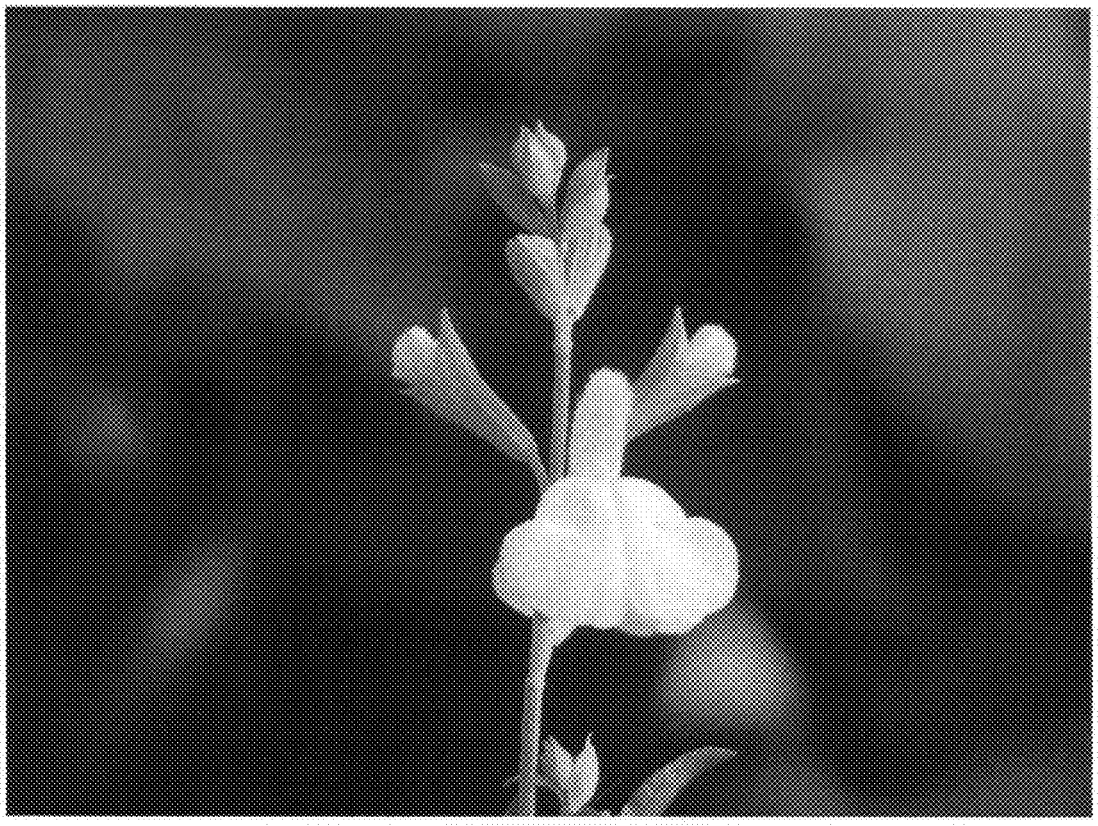
FIG. 3 depicts a close-up view of an individual flower and flower buds of 'Elk White Ice'.

The following detailed descriptions set forth the distinctive characteristics of 'Elk White Ice'. Observations, measurements, values, and comparisons were collected in March and April, 2015 in Santa Barbara, Calif. from two to three-month old plants grown outdoors in full sun in quart sized containers in Elk, Calif., with one pinch after initial cutting establishment and without any chemical growth regulators. Plants were transferred to Santa Barbara, Calif. when in bud and observed through flowering. Color determinations were made in accordance with The 2007 Royal Horticultural Society Colour Chart from London England, except where general color terms of ordinary dictionary significance are used.

Classification:

*Family*.—Lamiaceae.

*Genus*.—*Salvia*.

*Species*.—*Greggii*×*S. microphylla*.

*Common name*.—Sage.

Parentage:

*Female parent*.—*Salvia greggii* 'Texas Wedding' (unpatented).

*Male parent*.—*Salvia microphylla* 'Robin Middleton' (unpatented).

Plant:

*Propagation method*.—Softwood tip cuttings.

*Rooting system*.—Fine and fibrous.

*Vigor*.—Moderate vigor.

*Time to develop roots*.—5 days are needed for a cutting to develop roots at recommended rooting temperature of 20° to 22° Centigrade.

*Crop time*.—Approximately 12 weeks are required to produce a budded and flowering plant in a quart container from a rooted cutting.

*Suggested container size*.—Quart to 1 gallon container.

*Use*.—Ornamental for use as a landscape plant or container plant.

*Type*.—Perennial.

*Overall dimensions*.—After one year's growth in a 3.5 inch container: 30 cm to 35 cm in height, including the inflorescence, and 15 cm to 20 cm in width.

*Cultural requirements*.—Grow in full sun with moderate water and well-draining soil.

*Hardiness*.—USDA Zone 7. Further testing may indicate Zone 6.

*Form*.—Bush.

*Growth habit*.—Compact, erect.

*Blooming season*.—From one month after breaking spring dormancy to first frost.

*Lastingness of blooms*.—Inflorescence has some flower for 14 days, individual flowers last for 2 to 3 days.

Stems (below first pinch):

*Length*.—1 cm to 2 cm.

*Diameter*.—4 mm.

*Color*.—174C, bark where formed, 174A.

*Shape*.—Square, edges rounded.

*Texture*.—Rough where lignified.

Branches and secondary branches:

*Quantity*.—3 to 4, each with two secondary branches at each node.

*Shape*.—Terete, becoming square (rounded edges) towards inflorescence.

*Length*.—18 cm to 22 cm. Secondary branches 12 cm to 14 cm.

*Width*.—3.0 mm, sub-branches 1.5 mm to 2.0 mm.

*Internode length* (*branches and secondary branches*).—1.8 cm to 2.0 cm.

*Color*.—N170B close to stem, becoming green 145B towards apex.

Leaves:

*Type, arrangement*.—Simple, opposite.

*Attachment*.—Petiolate.

*Quantity per branch*.—Typically, 6 pairs on each branch, 4 pairs on each sub-branch.

*Shape*.—Elliptic.

*Length*.—26 mm.

*Width*.—13 mm.

*Margin*.—Weakly undulating, very shallowly crenulate, entire towards base.

*Thickness*.—Slightly fleshy.

*Venation*.—Pinnate, midrib slightly sulcate.

*Texture*.—Adaxial surface: Glabrous, glossy. Abaxial surface: Glabrous, semi-glossy.

*Color*.—Adaxial surface: 143A. Abaxial surface: 143C.

*Apex*.—Acute.

*Base*.—Cuneate.

*Fragrance*.—Pleasant sage fragrance when rubbed.

*Stipules*.—Present in pairs at each leaf axil. Small, elliptic, 9 mm in length, 3.5 mm in width. Petioles 1.5 mm in length, 0.5 mm in diameter. All other characteristics same as leaves.

Petiole:

*Shape*.—Terete.

*Length*.—8 mm.

*Width*.—1 mm.

*Texture*.—Puberulent.

*Color*.—144C.

Peduncle:

*Length*.—1.5 cm.

*Shape*.—Square with rounded edges.

*Width*.—1.0 mm to 1.2 mm.

*Texture*.—Puberulent.

*Color*.—145B.

Inflorescence:

*Type*.—Terminal raceme. Flowers arranged in pairs, opposite, each pair rotate by 90 degrees.

*Length*.—7.0 cm to 9.0 cm.

*Diameter*.—5 cm.

Pedicel:

*Length*.—4 mm.

*Width*.—0.8 mm.

*Texture*.—Puberulent.

*Color*.—145B.

Calyx:

*Shape*.—Campanulate, flared toward the apex.

*Length*.—11 mm.

*Height*.—6 mm.

*Width*.—3 mm.

Sepals:

*Quantity*.—2, one upper, one lower, substantially longitudinally fused.

*Length*.—11 mm.

*Width*.—6 mm when flattened.

*Shape*.—Cymbiform.

*Apex*.—Acuminate.

*Base*.—Truncate.

*Margin*.—Entire.

*Texture*.—Adaxial surface: Puberulent, longitudinally ribbed. Ribs 1 mm apart, raised less than 0.1 mm. Abaxial surface: Glabrous, longitudinal depressions.

*Color*.—Adaxial surface: 145B, ribs 145A. Abaxial surface: 145C.

Flowers:

*Quantity.*—10 to 12 arranged in opposite pairs.

*Shape.*—Tubular, two-lipped.

*Fragrance.*—Pleasant sage fragrance.

Bud (as emerges from calyx, before petals differentiated):

*Shape.*—Ellipsoidal.

*Length.*—4 mm to 5 mm.

*Width.*—3 mm to 4 mm.

*Texture.*—Pubescent, especially apex which already bears cluster of hairs of upper petal lip.

*Color.*—155A.

Corolla:

*Shape.*—Tubular proximally to two-lipped distally, lower lip attitude is downward, at an angle of 90 degrees to the corolla tube.

*Length.*—1.5 cm.

*Width.*—3 mm.

*Texture.*—Glossy, glandular.

*Color* (*both surfaces*).—NN155A, translucent.

Petals:

*Quantity.*—2.

*Arrangement.*—One upper petal hooded and one lower petal which appears as a lip which terminates with two fused orbicular lateral lobes.

*Upper petal.*—Shape: Hooded. Length: 9 mm to 10 mm. Width: 4 mm. Texture: Adaxial surface: Puberulent. Abaxial surface: Glabrous, with two longitudinal ribs. Apex: Rounded, with cluster of fine hairs approximately 1 mm in length, color 155A. Base: Truncate with lower lip at corolla mouth. Margin: Smooth, entire. Color (both surfaces): 155A.

*Lower petal, lip and lateral lobes.*—Shape: Lip rhomboid, lateral lobes orbicular, substantially fused to lip and to each other. Length: 13 mm. Width: 14 mm to 16 mm. Texture (both surfaces): Glabrous, semi-glossy. Apex: Rounded. Base: Truncate. Margin: Gently undulating. Color (both surfaces): NN155D.

*Floral bracts.*—Absent in repeated observations.

Reproductive organs:

*Stamens.*—Quantity: 1, comprised of two connected filaments, fused at base and longitudinally. Length: 12 mm. Color: NN155C.

*Filament.*—Length: Each filament is 12 mm, fused for 5 mm and free for 7 mm. Color: NN155C.

*Anther.*—Length: 1.2 mm. Width: 0.5 mm. Color: 163B.

*Pollen.*—Amount: Sparse. Color: 163B.

*Pistil.*—Quantity: 1. Stigma: Shape: Asymmetrically forked. Length: Longer fork 3 mm, strongly recurved; shorter fork 1.5 mm, gently recurved. Width: 0.5 mm. Color: NN155C. Style: Length: 24 mm. Color: NN155C, translucent.

*Ovary* (*only observed unfertilized, one pair of immature achenes*).—Length: 2 mm. Width: 1 mm. Color: 10B, achenes 8A.

Seed set: Rarely observed. Where present, one or two seeds per flower pollinated; shape is ovoid, with a length of 2 mm to 3 mm and a diameter of 1.5 mm. Color ranges between grey- brown 199B and dark brown N200A. Surface is smooth and glossy.

Disease and pest susceptibility: Susceptible to sucking insects when stressed. Generally outgrows most bacterial and viral infections. Resistant to deer and rabbit grazing.

Drought tolerance: Drought tolerant.

COMPARISON WITH PARENTAL LINES AND KNOWN VARIETY

'Elk White Ice' is distinguishable from the female parent, 'Texas Wedding' as follows: Whereas both 'Elk White Ice' and the female parent 'Texas Wedding' exhibit white flowers, 'Elk White Ice' is a smaller plant with significantly greater branching in comparison to plants of 'Texas Wedding' which seldom branch and are therefore less suitable for commercial production and consumer appeal.

'Elk White Ice' is distinguishable from the male parent, 'Robin Middleton' as follows: Whereas the flowers of 'Elk White Ice' are pure white in color, the flowers of the male parent 'Robin Middleton' are soft light pink in color. In addition, when compared with 'Robin Middleton', plants of 'Elk White Ice' are smaller and bear smaller, rounder and deeper green colored leaves. Finally, plants of 'Elk White Ice' exhibit a denser branching habit with more flowers and a longer flowering period.

'Elk White Ice' is similar to *Salvia* Plant Named 'EGGBEN006' (U.S. Plant Patent Publication No. 2014/0345026), however whereas 'Elk White Ice' has pure white flowers, 'EGGBEN006' has bright white flowers with a slight flush of red.

I claim:

1. A new and distinct cultivar of *Salvia* plant named 'Elk White Ice' as described and illustrated herein.

* * * * *